(12) United States Patent
Lin et al.

(10) Patent No.: US 8,906,955 B2
(45) Date of Patent: Dec. 9, 2014

(54) USE OF ADRENERGIC BETA-3-RECEPTOR AGONISTS IN ANTI-AGING

(71) Applicants: Shuguang Lin, Guangzhou (CN); Meng Zheng, Guangzhou (CN)

(72) Inventors: Shuguang Lin, Guangzhou (CN); Meng Zheng, Guangzhou (CN)

(*) Notice: Subject to any disclaimer, the term of this patent is extended or adjusted under 35 U.S.C. 154(b) by 0 days.

(21) Appl. No.: 13/754,600

(22) Filed: Jan. 30, 2013

(65) Prior Publication Data

US 2013/0197074 A1 Aug. 1, 2013

(30) Foreign Application Priority Data

Jan. 30, 2012 (CN) .......................... 2012 1 0020843

(51) Int. Cl.
| | | |
|---|---|---|
| A61K 31/38 | (2006.01) | |
| A61K 31/335 | (2006.01) | |
| A61K 31/36 | (2006.01) | |
| A61K 31/19 | (2006.01) | |
| A61K 31/18 | (2006.01) | |
| A61K 31/195 | (2006.01) | |
| A61K 31/138 | (2006.01) | |
| A61K 31/357 | (2006.01) | |
| A61K 31/426 | (2006.01) | |

(52) U.S. Cl.
CPC ............... *A61K 31/195* (2013.01); *A61K 31/18* (2013.01); *A61K 31/357* (2013.01); *A61K 31/426* (2013.01); *A61K 31/36* (2013.01); *A61K 31/138* (2013.01)
USPC ........... 514/438; 514/452; 514/464; 514/557; 514/601

(58) Field of Classification Search
CPC ..... A61K 31/18; A61K 31/19; A61K 31/357; A61K 31/36; A61K 31/426
USPC .......................... 514/438, 452, 464, 557, 601
See application file for complete search history.

(56) References Cited

FOREIGN PATENT DOCUMENTS

WO WO 2011075777 A1 * 6/2011

OTHER PUBLICATIONS

Gibbs et al., "Memory loss caused by β-amyloid protein is rescued by a β3-adrenoceptor agonist", Neurobiology of Aging, vol. 31, No. 4, pp. 614-624 (2010).*

* cited by examiner

*Primary Examiner* — Kevin E Weddington
(74) *Attorney, Agent, or Firm* — Muncy, Geissler, Olds & Lowe, P.C.

(57) ABSTRACT

A method for treating an aging-related disease is disclosed comprising administering to a subject a pharmaceutical composition comprising an adrenergic beta-3-receptor agonist.

4 Claims, 7 Drawing Sheets

USE OF ADRENERGIC BETA-3-RECEPTOR AGONISTS IN ANTI-AGING

CROSS-REFERENCE TO RELATED APPLICATION

The present invention claims priority from Chinese application number 201210020843.9 filed on Jan. 30, 2012, the disclosure of which is incorporated herein by reference.

FIELD OF THE INVENTION

The present invention relates to a new usage of adrenergic beta-3-receptor (ADRB 3) agonists, and in particular to its usage in anti-aging or preparation of anti-aging medicaments.

BACKGROUND OF THE INVENTION

Adrenergic beta-3-receptor, also known as beta-3 adrenergic receptor or beta-3 adrenoreceptor, a beta-adrenergic receptor, is located mainly in adipose tissue and is involved in the regulation of lipolysis and thermogenesis. ADRB 3 activating drugs could theoretically be used as weight-loss agents, but are limited by the side effect of tremors. Some ADRB 3 agonists have demonstrated antistress effects in animal studies, suggesting they also have a role in the CNS. Beta-3 receptors are found in gallbladder, urinary bladder, and in brown adipose tissue. Their role in gallbladder physiology is unknown, but they are thought to play a role in lipolysis and thermogenesis in brown fat. Our search did not reveal any reports about effect of beta-3 receptors in genesis and development of age-related diseases.

Energy metabolism and oxidative stress play an important role in genesis of aging. Mitochondrion serves as a plant for production of both ATP and reactive oxygen species (ROS). Anti-oncogene TP53 plays a key role in aging regulation and cell programmable rearrangement, which can activate DNA repair proteins when DNA has sustained damage. However, hyperactivity of p53 would cause progeria of stem cell. SIRT1 is an enzyme that deacetylates proteins that contribute to cellular regulation, such as p53, and thus is involved in aging regulation. Mammalian target of rapamycin, also known as mTOR, plays an importance role in many aspects including cell growth, cell proliferation and cell cycle as well as cell senescence.

SUMMARY OF THE INVENTION

In the work leading to the present invention, the inventors surprisingly found that the adrenergic beta-3-receptor (hereinafter sometimes referred to as the β3 receptor) is a key receptor involved in regulation of signaling pathways of SIRT1, p53, mTOR and microRNA-16. Based on this finding, the present invention provides a new usage of adrenergic β3 receptor agonists in treating mTOR/SIRT1/p53 signaling pathways related diseases, including Alzheimer's disease, tuborous sclerosis, pulmonary hypertension, myocardial fibrosis, hepatic cirrhosis, renal failure, therioma and etc. The present invention further provides a new usage of adrenergic β3 receptor agonists in anti-aging or treatment of aging-related diseases. The present invention yet provides the usage of adrenergic β3 receptor agonists in improvement of efficiency of induced pluripotent stem cells (iPS).

The anti-aging effect of β3 receptor agonists is achieved by at least one of the following mechanisms, (a) inhibition of mitophagy, protection of mitochondrial membrane potential, promotion of mitochondrial fusion, activation of voltage-dependent anion channel (VDAC), reduction of reactive oxygen species and reduction of lipofuscin; (b) activation of Rheb/SIRT1/FOXO4 pathway, enabling deacetylation of p53; (c) agonisting of p62/mTORC2/4EBP1 pathway, promote of binding of mTORC2 with α-Tubulin, and promote of binding of phosphorylated mTOR (Ser2448) to centrosomes at both poles of spindle apparatus; (d) stabilization of spindle apparatus to increase mitosis; (e) activation of hypoxia inducible factor-1α(HIF1α)/hexokinase II pathway to enhance glycolysis; (f) downregulation of expression of miR-16-1 and miR-15a.

The inventor further found that agonisting of β3 receptor can increase mTOR-Rictor complex (mTORC2) and that β3 receptor agonists can be used as mitophagy antagonists.

The β3 receptor agonists used in the present invention include any compound that is able to excite the β3 receptor. Representative agonists suitable for use in the present invention include but not limited to BRL 37344, SR58611A, TAK2677, N25984, and the like.

The β3 receptor agonists used in the present invention can be prepared by conventional methods and provided in suitable form, including tablets, capsules, granules, controlled release formulations, injectable formulations and others.

The present invention propose to use β3 receptor agonists as drugs or a part of drugs for treating Alzheimer's disease, tuberous sclerosis, pulmonary hypertension, myocardial fibrosis, hepatic cirrhosis, renal failure, therioma and etc. Futhermore, β3 receptor agonists can be used as an SIRT 1 angonist for anti-aging treatment.

The present invention propose to use β3 receptor agonists to improve production efficiency of induced pluripotent stem cell so as to slow down cell senescence and aging of adipose-derived stem cells as well as cardiac stem cells.

The present invention reveals the signaling pathway of beta-3 adrenergic receptor, i.e., its regulation of expression and activity of mTOR, SIRT1, and p53 proteins, which is meaningful to the research of generation and development of diseases such as tumors, metabolic diseases, diseases of immune system and aging-related diseases. The beta-3 adrenergic receptor can be served as a target to treat those diseases by regulation of the receptor.

DETAILED DESCRIPTION OF THE INVENTION

Definitions

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" include any and all combinations of one or more of the associated listed items. It will be further understood that the terms "comprises" "comprising" "includes" and/or "including" when used herein, specify the presence of stated features, integers, steps, operations, elements, and/or components, but do not preclude the presence or addition of one or more other features, integers, steps, operations, elements, components, and/or groups thereof.

An "agonist" is a chemical that binds to a receptor of a cell and triggers a response by that cell. Agonists often mimic the action of a naturally occurring substance and generate typical physiological function of that naturally occurring substance. Whereas an agonist causes an action, an antagonist blocks the action of the agonist and an inverse agonist causes an action opposite to that of the agonist. An agonist can be a selective agonist which is selective for one certain type of receptor.

Beta-adrenergic agonists are a class of sympathomimetic agents which act upon the beta adrenoreceptors. In general, pure beta-adrenergic agonists have the opposite function of beta blockers. Beta adrenoreceptor agonist ligands mimic the action of epinephrine and norepinephrine signaling in the heart, lungs and smooth muscle tissue, with epinephrine being the highest affinity. The activation of β1, β2 and β3 activates the enzyme, adenylate cyclase. This in turn leads to the activation of the secondary messenger cyclic adenosine monophosphate and induces smooth muscle relaxation and contraction of the cardiac tissue. Adrenergic beta-3-receptor (ADRB 3) agonists include but not limited to CL316243, N-5984, BMS-194449, BMS-196085, CP114271, CP80625, BRL 37344, SR58611A, TAK2677, N25984.

EXAMPLES

Example 1

Figure 1:
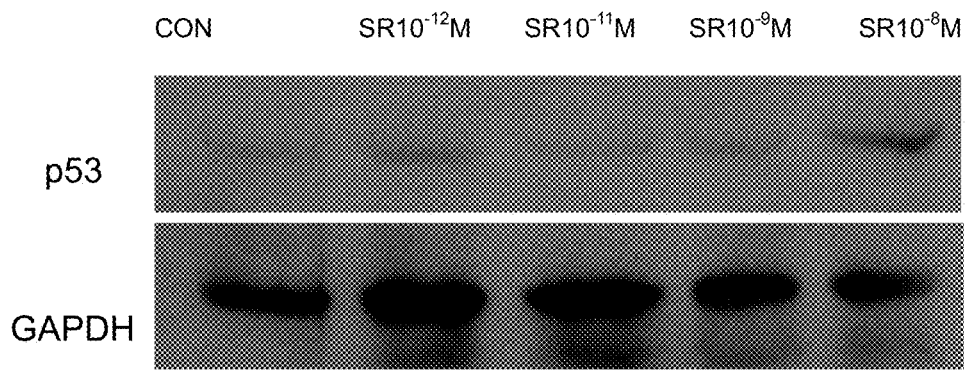
FIG. 1. SR59230A increased expression level of p53 in MCF-7 cells.
Figure 2:
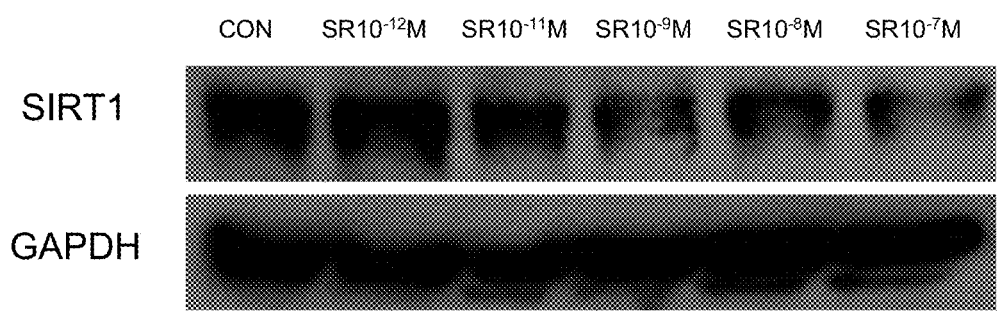
FIG. 2. SR59230A decreased expression level of SIRT1 in MCF-7 cells.

MCF-7 cells were treated with SR59230A at different concentrations. After 24 h, the cells were lysed to extract total protein. The protein concentration was determined by BCA method. 10 μg of the protein was used to perform 10% SDS PAGE, and then transferred to a PVDF membrane. The membrane was blocked for 1 h with TBST (10 mmol/L Tris HCl, pH 7.5, 150 mmol/L NaCl, 0.1% Tween 20) containing 4% fat-free milk, and incubated overnight with p53 antibody (1:1000) and SIRT1 antibody (1:1000) at 4° C. The membrane was further incubated with secondary antibodies for 1 h after washing, followed by ECL color development. The same procedure is repeated 3 times. The gray values of protein bands were obtained through Fluorchem 8900 software and the ratio of target band to reference band (GAPDH) was calculated. Results are shown in FIGS. 1 and 2, wherein the expression level of p53 is increased as the increase of SR59230A concentration, while SIRT1 is decreased.

Example 2

Figure 3:
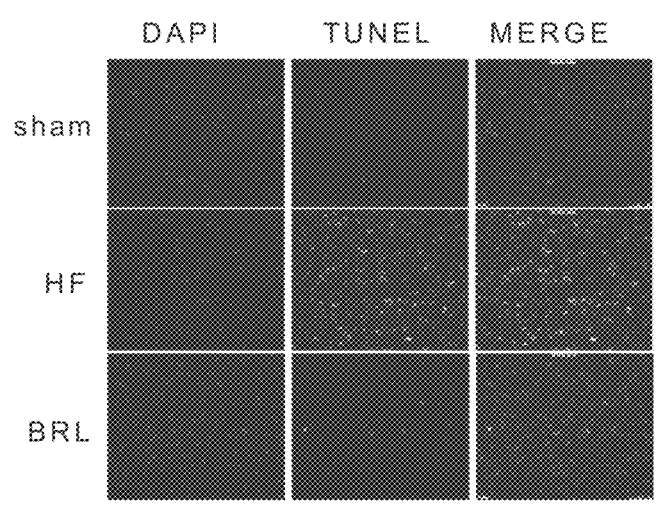
FIG. 3. BRL37344 decreased cardiomyocytes apoptosis of heart failure rats.
Figure 4:
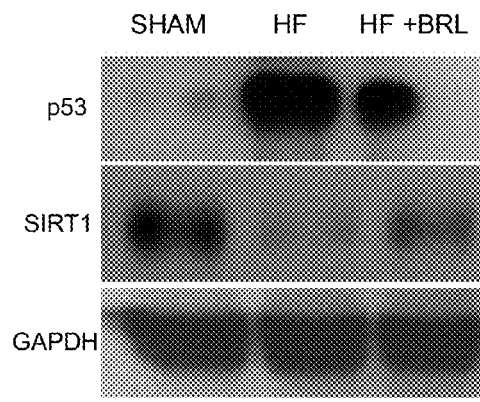
FIG. 4. BRL37344 decreased p53 level and increases SIRT1 in rat myocardia.
Figure 5:
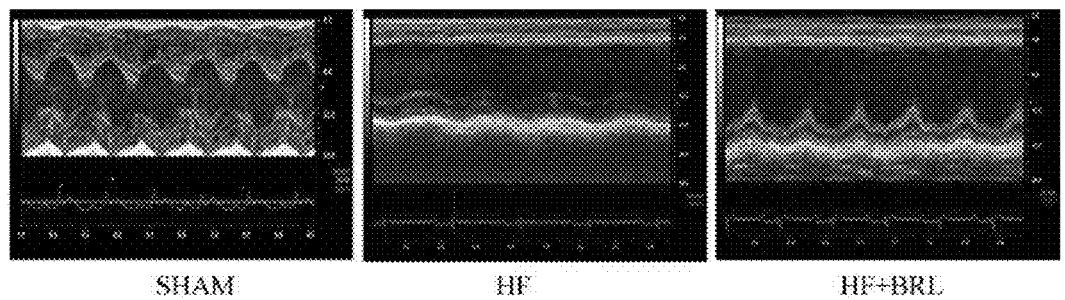
FIG. 5. BRL37344 improved cardiac function of heart failure rats.

In rat myocardial infarction models, activation of the β-3 receptor could increase level of SIRT1 in cardiomyocyte, inhibit expression of p53, improve the cardiac function and achieve anti-apoptosis effect. The myocardial infarction model was created by ligation of anterior descending branch of rat left coronary artery. BRL37344 was intraperitoneally injected at 1 mg/kg/day, and heart B-ultrasonography was performed after 4 weeks. Heart tissue was determined for apoptosis (tunel method) and expression levels of SIRT1 and p53 (western blot). The ratio of left ventricular weight to body weight (LVW/BW) is determined. It can be seen from the results shown in FIGS. 3 to 5, that BRL37344 decreases p53 expression, cardiac cell apoptosis, and value of LVW/BW of heart failure rat, increases SIRT1 expression, alleviate cardiac hypertrophy and improve cardiac function.

Example 3

Figure 6:
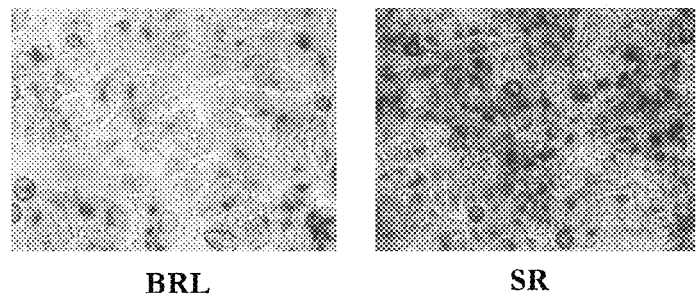
FIG. 6. Staining of β3-galactosidase in adipose-derived stem cells.

Blockage of the β-3 receptor could increase level of β-galactosidase in adipose-derived stem cells and promote stem cell aging. BRL37344 and SR59230A were used to treat adipose-derived stem cells of rats each at $10^{-7}$ M. After 24 h, cells were fixed using paraformaldehyde, and stained and photographed according to the specification of β-Galactosidase Staining Kit. Results were shown in FIG. 6. BRL37344 decreases the level of β-galactosidase in adipose-derived stem cells compared with SR59230A, indicating agonisting of adrenergic β3 receptors of adipose-derived stem cells achieves anti-aging effect.

Example 4

Figure 7:
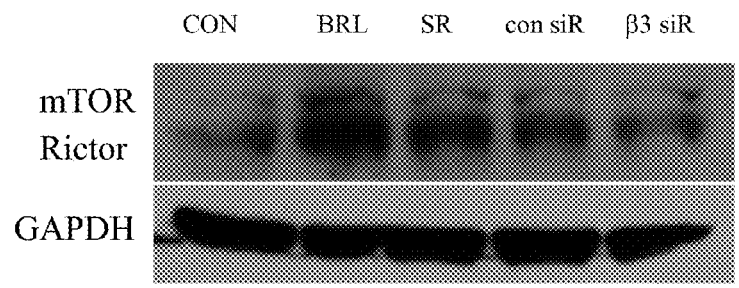
FIG. 7. BRL37344 increased level of mTOR/Rictor complex.

Activation of the β3 receptor could increase mTOR/Rictor complex in MCF-7 cells. shRNA of β3 adrenergic receptor, control shRNA, BRL37344 and SR59230A was used to treat rat cardiomyocyte each at $10^{-7}$ M. After 24 h, total protein was extracted and subjected to western blot to determine the expression amount of mTOR and Rictor proteins. The results were shown in FIG. 7. BRL37344 increases Mtor/Rictor complex while β3 adrenergic receptor shRNA significantly decreases mTOR/Rictor complex, when compared to the control shRNA.

Example 5

Figure 8:
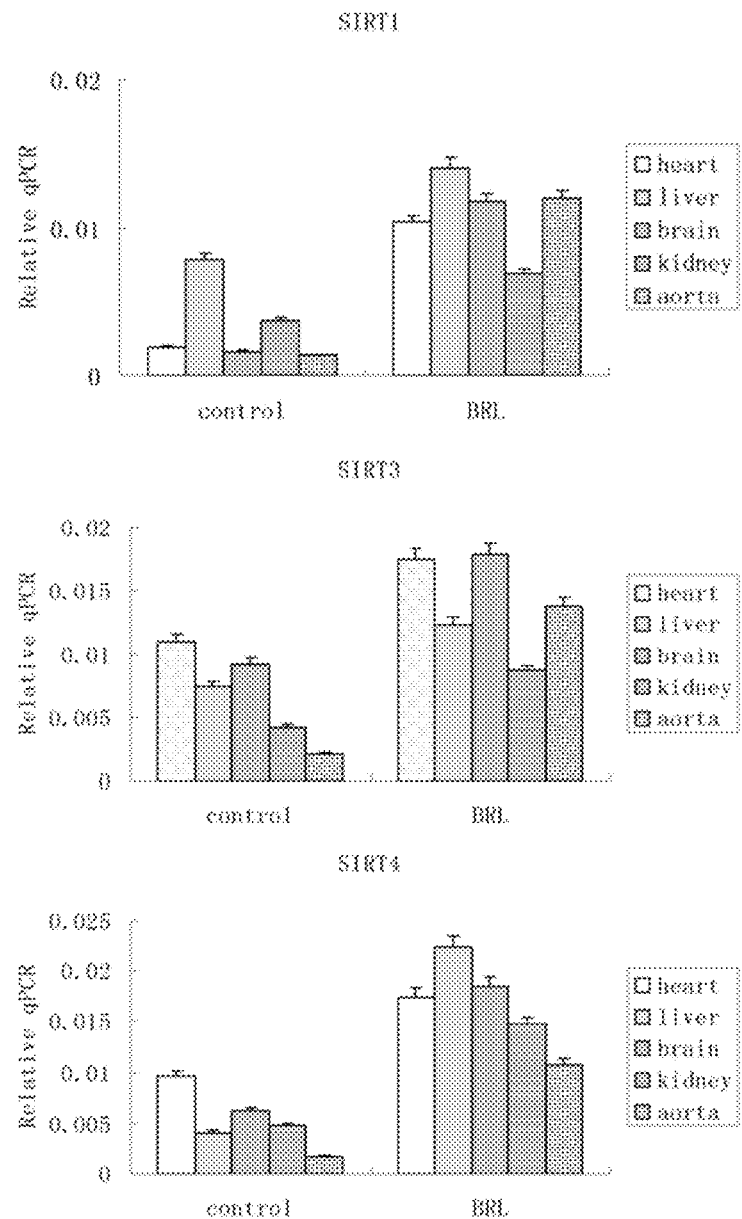
FIG. 8. Results of quantitative PCR for SIRT 1, 3, and 4.

Activation of the β3 receptor could increase the expression of SIRT1, SIRT3 and SIRT4 in heart, liver, brain, kidney and aorta of aging rats. Twenty 12-month male SD rats were randomly divided into 2 groups. The rats were intraperitoneally injected with BRL37344 at 100 nmol for each rat, qd, 2 weeks. The rats in control group were administrated with solvents of same volume. The rats were sacrificed to obtain heart, liver, brain, kidney and aorta, followed by total RNA extraction. The RNA was then reversely transcribed, followed by quantitative PCR to detect gene expression of SIRT1, SIRT3 and SIRT4. The results were shown in FIG. 8. Compared to the control group, BRL37344 increases the expression of SIRT1, SIRT3 and SIRT4 in heart, liver, brain, kidney and aorta.

Example 6

Figure 9:
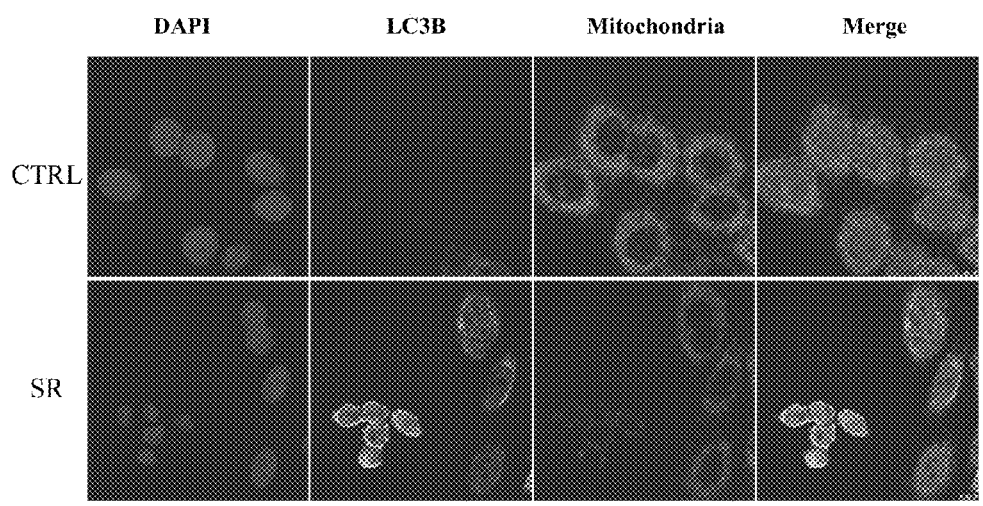
FIG. 9. Results of immunofluorescence double staining of MitoTracker/LC3B.
Figure 10:
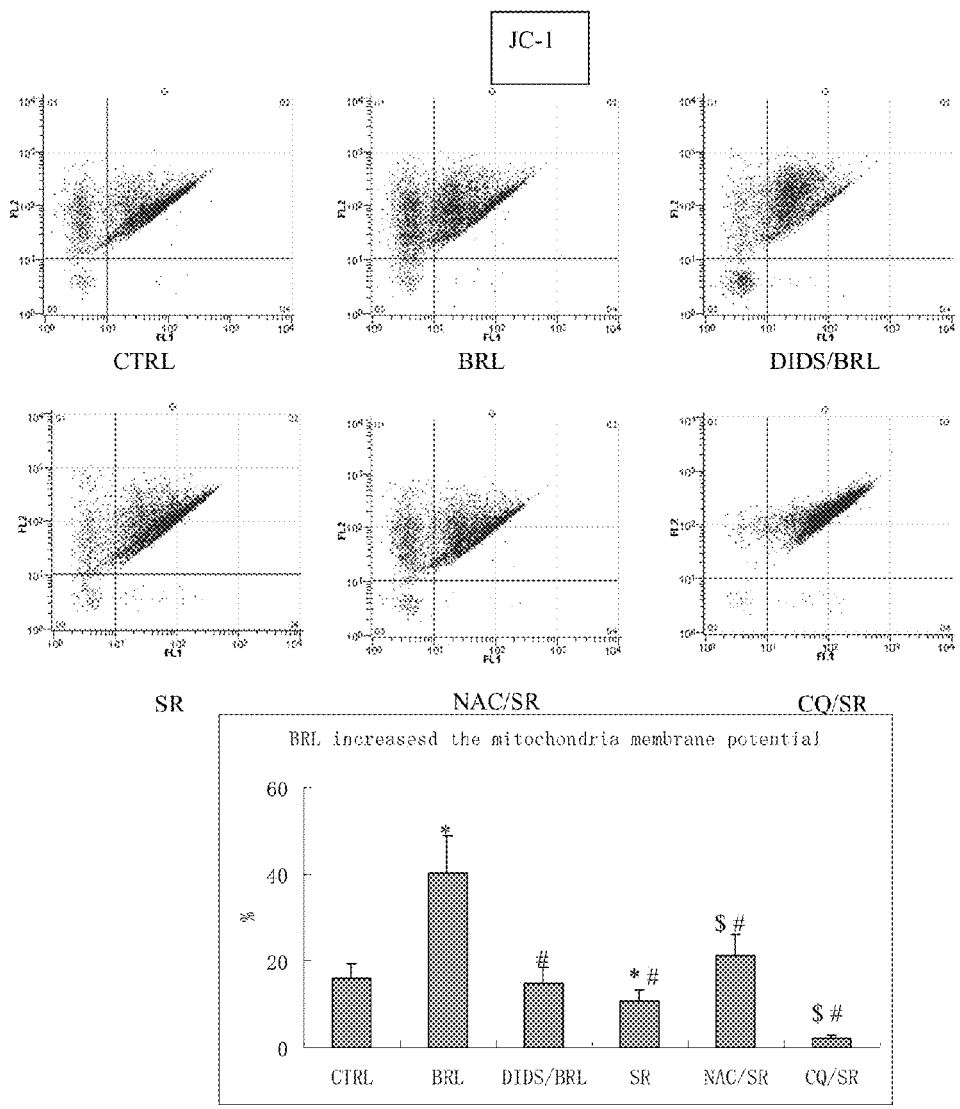
FIG. 10. Results of flow cytometry of JC-1.
Figure 11:
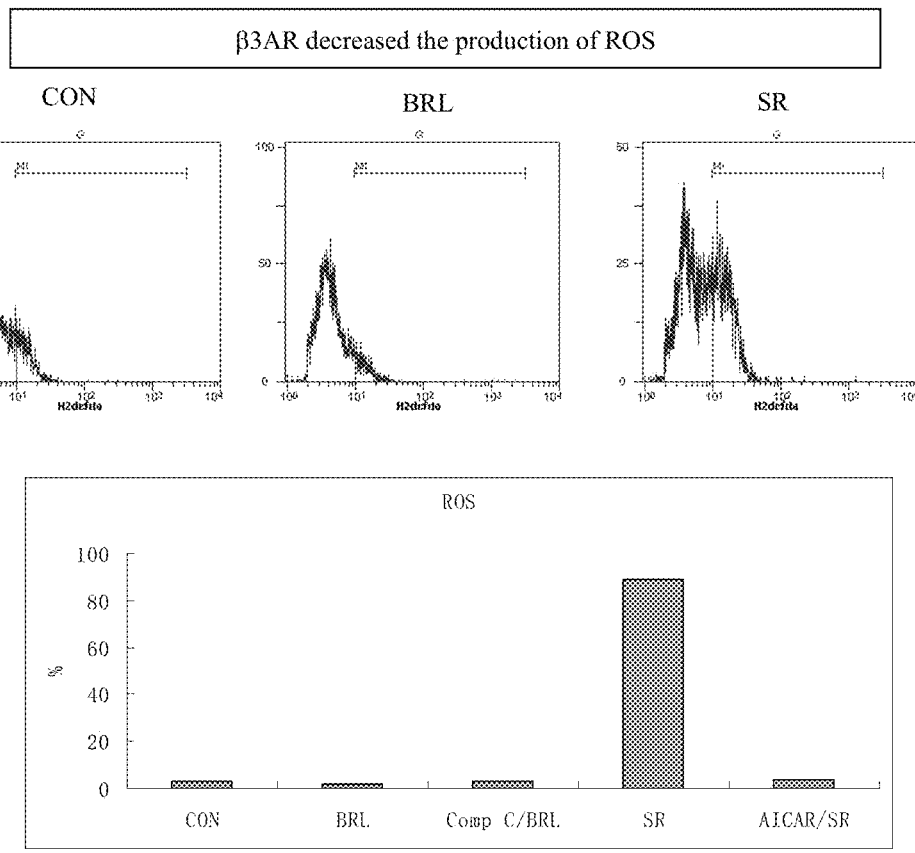
FIG. 11. H2DCFDA flow cytometry of reactive oxygen species.
Figure 12:
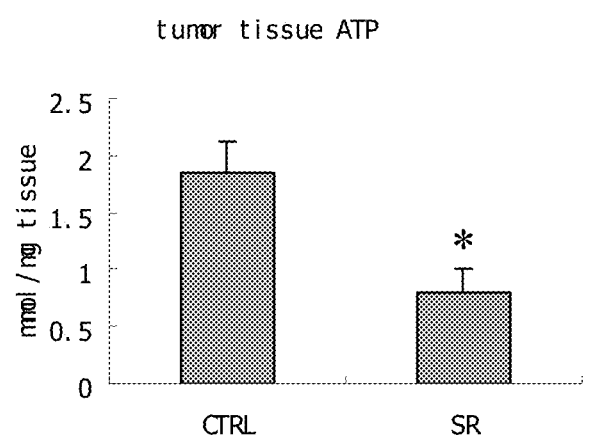
FIG. 12. ATP content in tumor tissue of naked tumor-bearing rats.

Activation of the β3 receptor could increase mitochondrial content of MCF7 cells. BRL37344 and SR59230A were used to treat MCF7 cells and naked tumor-bearing rats each at $10^{-7}$ M. The amount of mitochondrion was determined by MitoTracker probes. Mitochondrial membrane potential was determinded by JC1. The ROS content of the cells was determined by fluorescence probe H2DCFDA. ATP level was determined by ATP kit. MDC staining was determined by flowcytometer. GFP-LC3 eukaryotic expression vectors were used for transfection. The results showed that SR59230A decreases the content of mitochondrion and enhance mitophagy (FIG. 9). BRL37344 protected mitochondrial membrane potential (FIG. 10), reduced intracellular ROS content (FIG. 11), and increased intracellular ATP level (FIG. 12). SR59230A increased MDC staining, reduced mitochondrions, damaged mitochondrial membrane potential and promoted to form many bright and green fluorescent spots.

Example 7

Figure 13:
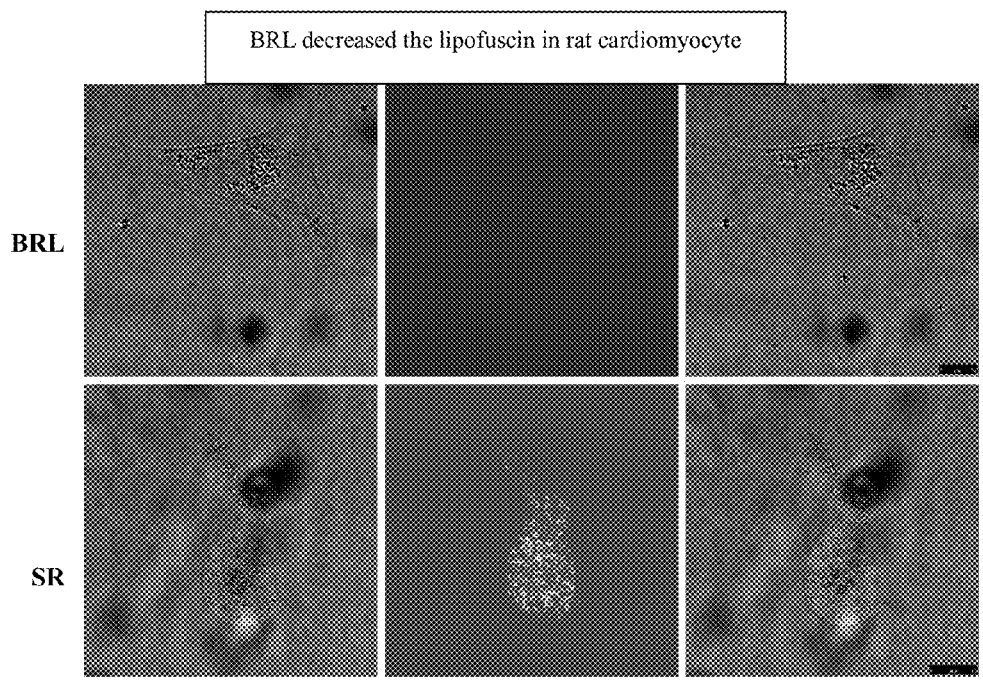
FIG. 13. Lipofuscin level in cardiomyocyte of rats.

Beta-3 receptor reduced amount of lipofuscin in cardiomyocyte. BRL37344 and SR59230A were used to treat cardiomyocyte each at $10^{-7}$ M. After 10 days, cells were observed under confocal microscope for lipofuscin. The results showed that BRL37344 significantly reduced lipofuscin (FIG. 13), indicating anti-aging effect.

Example 8

Figure 14:
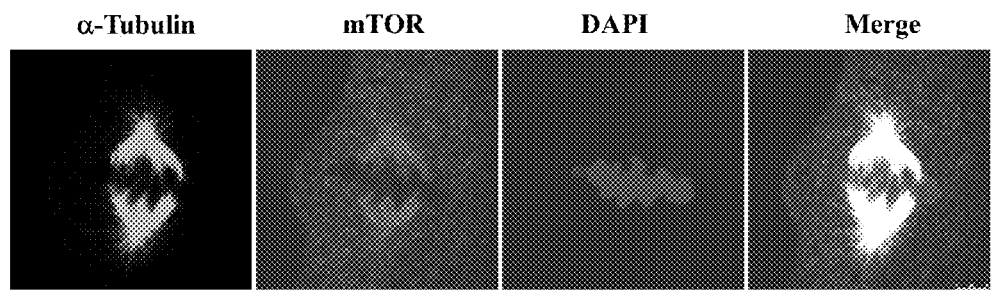
FIG. 14. Results of immunofluorescence double staining of mTOR/α-Tubulin.
Figure 15:
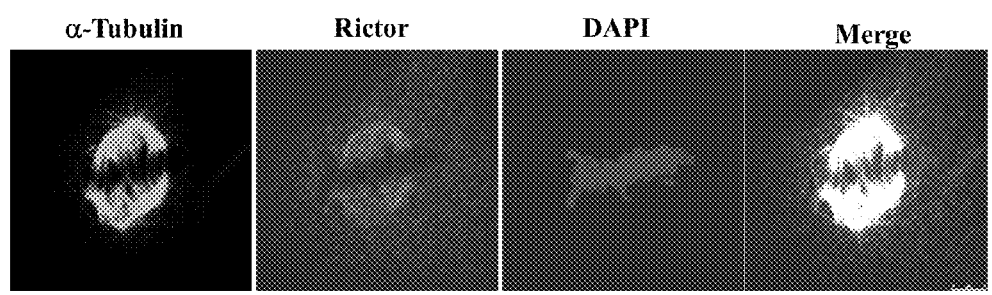
FIG. 15. Results of immunofluorescence double staining of Rictor/α-Tubulin.

Beta-3 receptor promoted binding of mTORC2 to α-Tubulin in spindle apparatus. BRL37344 was used to treat cardiac fibroblast of rats at $10^{-7}$ M. The cells were undergone mTOR/α-Tubulin immunohistochemical double staining and Rictor/α-Tubulin immunofluorescence double staining, and observed under confocal microscope. The results showed BRL37344 promoted binding of mTOR to α-Tubulin in spindle apparatus (FIG. 14) and Rictor to α-Tubulin (FIG. 15).

It should be understood that various example embodiments have been described with reference to the accompanying drawings in which only some example embodiments are shown. The present invention, however, may be embodied in many alternate forms and should not be construed as limited to only the example embodiments set forth herein.

What is claimed is:

1. A method for treating an aging-related disease, comprising administering to a subject in need of the treatment a pharmaceutical composition comprising an adrenergic beta-3-receptor agonist, wherein the aging-related disease is selected from a group consisting of myocardial fibrosis, renal failure, and therioma.

2. The method of claim 1, wherein the adrenergic beta-3-receptor agonist is selected from the group consisting of CL316243, N-5984, BMS-194449, BMS-196085, CP 114271, CP80625, BRL37344, SR58611A, TAK2677, and N25984.

3. The method of claim 1, wherein the adrenergic beta-3-receptor agonist is selected from the group consisting of BRL37344, SR58611A, TAK2677, and N25984.

4. The method of claim 1, wherein the aging-related disease is myocardial fibrosis.

* * * * *